United States Patent [19]
Suzuki et al.

[11] Patent Number: 5,880,309
[45] Date of Patent: Mar. 9, 1999

[54] PHENYLPHOSPHONIC ACID DERIVATIVE AND PRODUCTION PROCESS THEREFOR

[75] Inventors: Hideo Suzuki; Masafumi Nomura; Kenichi Tokunaga; Isao Hashiba, all of Funabashi, Japan

[73] Assignee: Nissan Chemical Industries, Ltd., Tokyo, Japan

[21] Appl. No.: 8,244

[22] Filed: Jan. 15, 1998

[30] Foreign Application Priority Data

Jan. 28, 1997 [JP] Japan .................................. 9-013806
Oct. 29, 1997 [JP] Japan .................................. 9-296715

[51] Int. Cl.$^6$ .................................. C07F 9/40; C07F 9/38
[52] U.S. Cl. .............................. 558/198; 558/125; 562/24
[58] Field of Search .................................. 558/125, 198; 562/24

[56] References Cited

U.S. PATENT DOCUMENTS 2,834,804   5/1958   Lecher et al. .
5,498,784   3/1996   Arnold et al. .

FOREIGN PATENT DOCUMENTS 27 45 982    4/1979   Germany .
A-6-24688    2/1994   Japan .
763992      12/1956   United Kingdom .

OTHER PUBLICATIONS

T. Shima et al., "Poly(ethylene terephthalate) Composite Fiber", Chemical Abstracts, pp. 74, vol. 72, No. 15, (1970).
B.C.M. Dorset, "Fiber–manufacturing Developments Assist Dryers and Finishers", Chemical Abstracts, vol. 65, No. 8 (1966).
The Journal of Organic Chemistry, vol. 35, No. 5, May 1970, p. 1691.
Chem. Ber. vol. 103, 1970, p. 2428.
Chemical Reviews, 1981, vol. 81, No. 4, p. 415.

*Primary Examiner*—Michael G. Ambrose
*Attorney, Agent, or Firm*—Oliff & Berridge, PLC

[57] ABSTRACT

A dialkyl dialkoxycarbonylphenylphosphonate which is useful as a resin modifier, a process for producing the same in high yield at a low cost, and a process for producing a dicarboxyphenylphosphonic acid in high yield at a low cost are described.

The process for producing a dialkyl dialkoxycarbonylphenylphosphonate comprises heating and reacting a dialkoxycarbonylphenyl halide with a trialkyl phosphate in the presence of a catalyst comprising an element of group VIII of the periodic table (such as an alumina supported palladium catalyst) and hydrolyzing the obtained dialkyl dialkoxycarbonylphenylphosphonate in the presence of an acid or base to produce a dicarboxyphenylphosphonic acid.

9 Claims, 7 Drawing Sheets

PHENYLPHOSPHONIC ACID DERIVATIVE AND PRODUCTION PROCESS THEREFOR

BACKGROUND OF THE INVENTION

1. Field of the Invention

The present invention relates to a dialkyl dialkoxycarbonylphenylphosphonate, a production process therefor and a process for producing a dicarboxyphenylphosphonic acid.

2. Related Art

Only dimethyl 2,3-dimethoxycarbonylphenylphosphonate represented by the following formula (V) is known as a dialkyl dialkoxycarbonylphenylphosphonate.

(V)

A process for producing this comprises obtaining 1,2-dimethoxycarbonyl-3-dimethoxyphosphonocyclohexa-1,4-diene as an intermediate through a Diels-Alder reaction between 1-(1,3-butadienyl)phosphonic acid and dimethyl acetylenedicarboxylate and aromatizing the obtained intermediate into dimethyl 2,3-dimethoxycarbonylphenyl phosphonate of interest using nitrobenzene and an activated carbon supported palladium catalyst. Although the Diels-Alder reaction is very interesting, it is not preferred and can not be employed for the industrial-scale production of dimethyl 2,3-dimethoxycarbonylphenylphosphonate because of its low reaction yield (Journal of Organic Chemistry, vol.35, pp.1691, 19703.

Dialkyl monoalkoxycarbonylphenylphosphonates obtained by an Arbuzov reaction are known. A process for producing these comprises reacting a trialkyl phosphite with a monoalkoxy carbonylphenyl halide using nickel chloride as a catalyst at a reaction temperature of 150° to 160° C. [Chem. Ber., vol.103, pp.2428, 1970, Chem. Rev. vol.81, pp.415, 1981 for the outline of the Arbuzov reaction]. However, there are unknown dialkyl dialkoxycarbonylphenylphosphonates produced by an Arbuzov reaction using a dialkoxycarbonylphenyl halide.

As a dicarboxyphenylphosphonic acid is known o-dicarboxyphenylphosphonic acid represented by the following formula (VI).

(VI)

A process for producing this comprises reacting o-xylene with phosphorus pentaoxide in an autoclave at a temperature of 270° C., reacting phosphorus oxychloride and phosphorus pentaoxide with the reaction product from which unreacted o-xylene has been removed to obtain o-dimethylphenylphosphonyl dichloride (isomer mixture). This o-dimethylphenylphosphonyl dichloride is chlorinated by exposure to ultraviolet light to obtain a chlorinated product thereof. An aqueous solution of potassium hydroxide is added to this chlorinated product to oxidize it while the reaction solution is maintained alkaline by an aqueous solution of potassium hydroxide and an aqueous solution of potassium permanganate, whereby o-dicarboxylphenylphosphonic acid is obtained [refer to the disclosure of U.S. Pat. No. 2,834,804].

However, it cannot be said that this process is a practical production process because the obtained o-dicarboxyphenylphosphonic acid is an isomer mixture, potassium permanganate must be treated after completion of the reaction, and special reaction devices such as a high-temperature and high pressure autoclave and a photochemical reaction device are required.

There is known a process for producing a substituted phenylphosphonic acid by hydrolyzing a dialkyl monoalkoxycarbonylphenylphosphonate obtained by an Arbuzov reaction with hydrochloric acid [Chem. Ber. vol.103, pp.2428, 1970]. However, there is unknown a process for producing a dicarboxyphenylphosphonic acid by hydrolyzing a dialkyl dialkoxycarbonylphenylphosphonate through an Arbuzov reaction using a dialkoxycarbonylphenyl halide.

The inventors of the present invention have paid attention to dialkyl dialkoxycarbonylphenylphosphonates which are useful as a resin modifier and have conducted intensive studies on dialkyl dialkoxycarbonylphenylphosphonates and a production process therefor. As a result, they have synthesized a novel dialkyl dialkoxycarbonylphenylphosphonate and have found a process for producing a dialkyl dialkoxycarbonylphenylphosphonate and a dicarboxyphenylphosphonic acid in high yield at a low cost. Thus, they have accomplished the present invention.

In the present invention, it has been found that a supported catalyst is excellent in yield and recovery as a catalyst.

SUMMARY OF THE INVENTION

It is an object of the present invention to provide a dialkyl dialkoxycarbonylphenylphosphonate useful as a resin modifier, a process for producing a dialkyl dialkoxycarbonylphenylphosphonate in high yield at a low cost, and a process for producing a useful dicarboxyphenylphosphonic acid in high yield at a low cost.

The process of the present invention for producing a dialkyl dialkoxycarbonylphenylphosphonate represented by the following general formula (I):

(I)

wherein $R^1$ and $R^2$ are each selected from the group consisting of alkoxycarbonyl groups having 1 to 10 carbon atoms, $R^3$ is selected from alkyl groups having 1 to 10 carbon atoms, and $R^1$, $R^2$ and $P(O)(OR^3)_2$ are substituted at arbitrarily selected different positions on a benzene ring, comprises reacting a dialkoxycarbonyphenyl halide represented by the following general formula (II):

(II)

wherein $R^4$ and $R^5$ are each selected from the group consisting of alkoxycarbonyl groups having 1 to 10 carbon atoms, X is a halogeno group, and $R^4$, $R^5$ and X are substituted at arbitrarily selected different positions on a benzene ring, with a trialkyl phosphite represented by the following general formula (III):

(III)

wherein $R^6$ is selected from the group consisting of alkyl groups having 1 to 10 carbon atoms, by heating in the presence of a catalyst comprising an element of group VIII of the periodic table.

The process of the present invention for producing a dicarboxyphenylphoshonic acid represented by the following general formula (IV):

wherein $R^7$ and $R^8$ are each a carboxyl group, and $R^7$, $R^8$ and $P(O)(OH)_2$ are substituted at arbitrarily selected different positions on a benzene ring, comprises reacting a dialkoxycarbonylphenyl halide represented by the following general formula (II):

wherein $R^4$ and $R^5$ are each selected from the group consisting of alkoxycarbonyl groups having 1 to 10 carbon atoms, X is a halogeno group, and $R^4$, $R^5$ and X are substituted at arbitrarily selected different positions on a benzene ring, with a trialkyl phosphite represented by the following general formula (III):

$$(R^6O)_3P \qquad (III)$$

wherein $R^6$ is selected from the group consisting of alkyl groups having 1 to 10 carbon atoms, by heating in the presence of a catalyst comprising an element of group VIII of the periodic table to obtain a dialkyl dialkoxycarbonylphenylphosphonate represented by the following general formula (I):

wherein $R^1$ and $R^2$ are each selected from the group consisting of alkoxycarbonyl groups having 1 to 10 carbon atoms, $R^3$ is selected from the group consisting of alkyl groups having 1 to 10 carbon atoms, and $R^1$, $R^2$ and $P(O)(OR^3)_2$ are substituted at arbitrarily selected different positions on a benzene ring, and hydrolyzing the dialkyl dialkoxycarbonylphenylphosphonate in the presence of an acid or base.

DETAILED DESCRIPTION OF THE PREFERRED EMBODIMENTS

Figure 1:
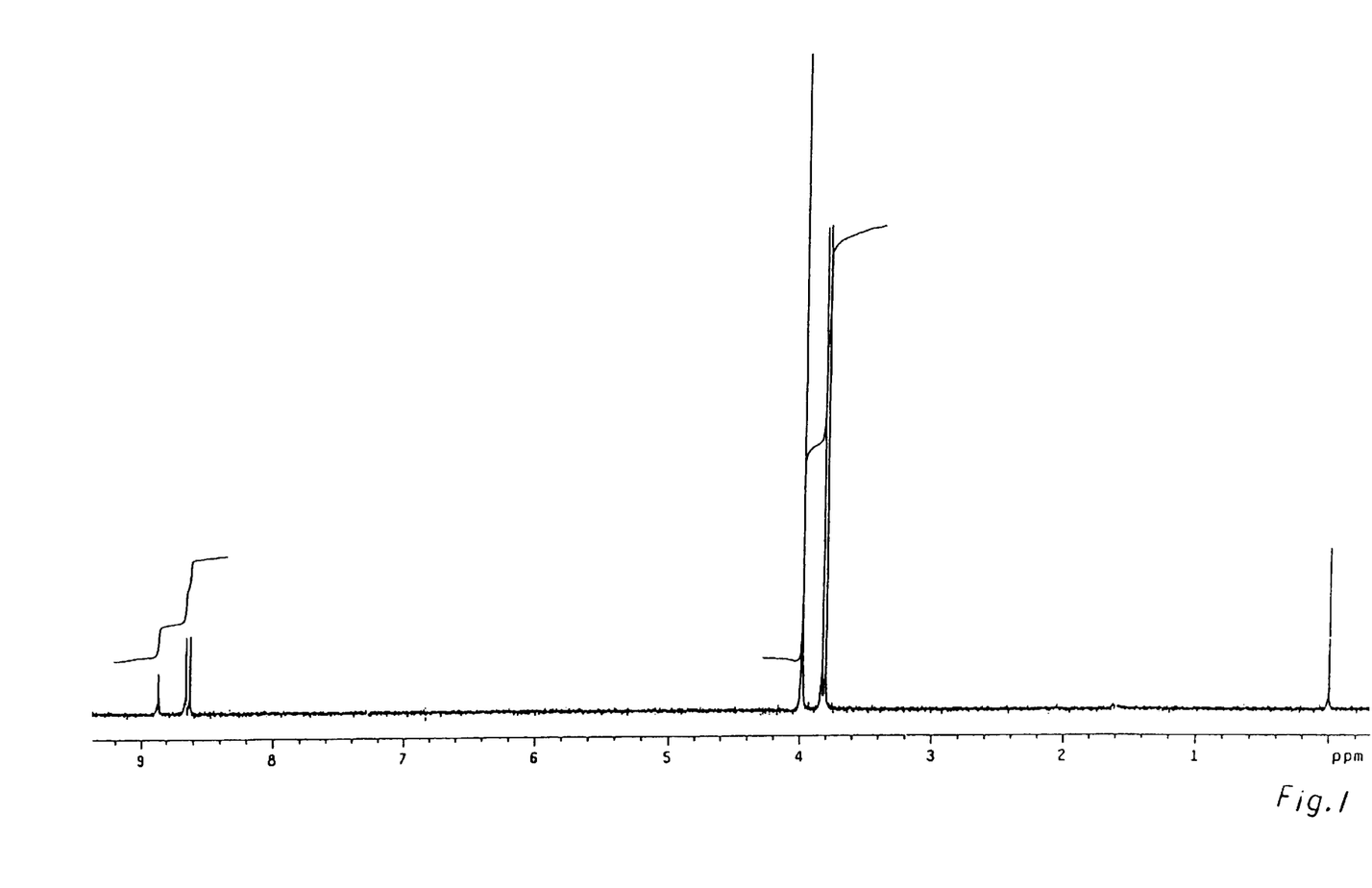
FIG. 1 is a $^1$H-NMR chart of dimethyl 3,5-dimethoxycarbonylphenylphosphonate obtained in Example 1.
Figure 2:
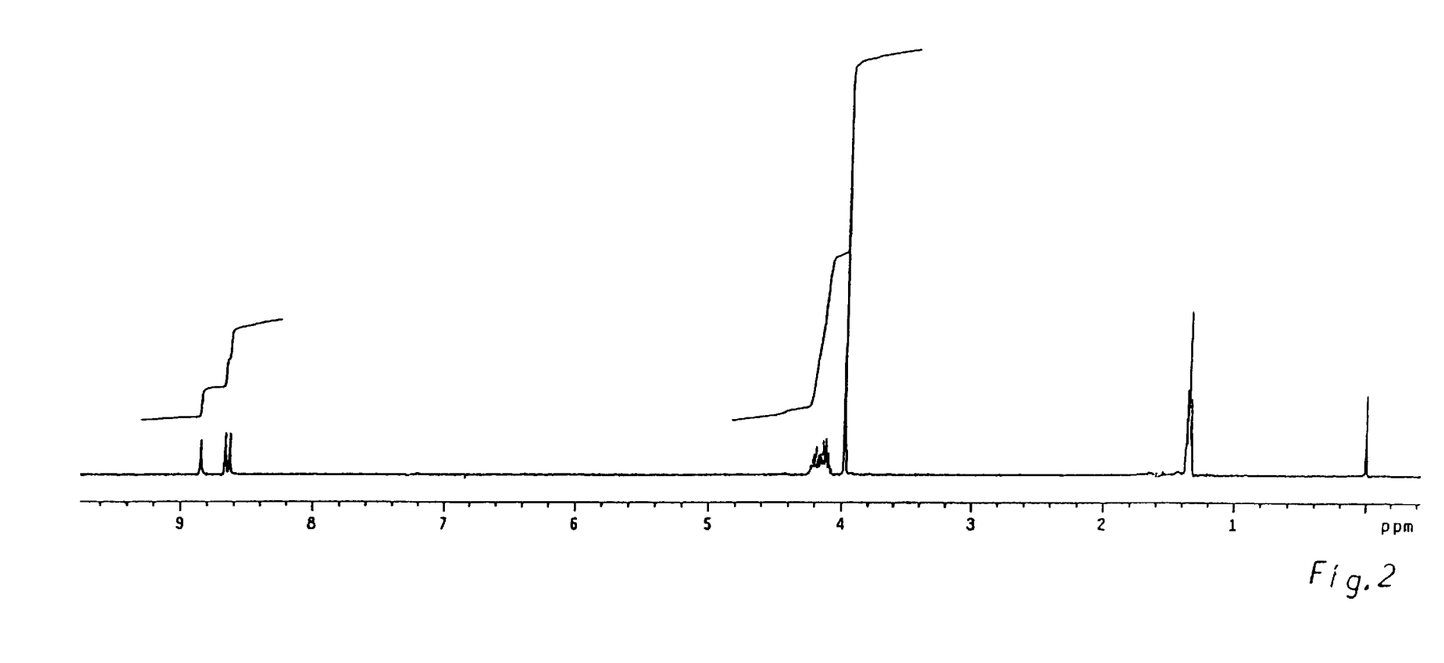
FIG. 2 is a $^1$H-NMR chart of diethyl 3,5-dimethoxycarbonylphenylphosphonate obtained in Example 2.
Figure 3:
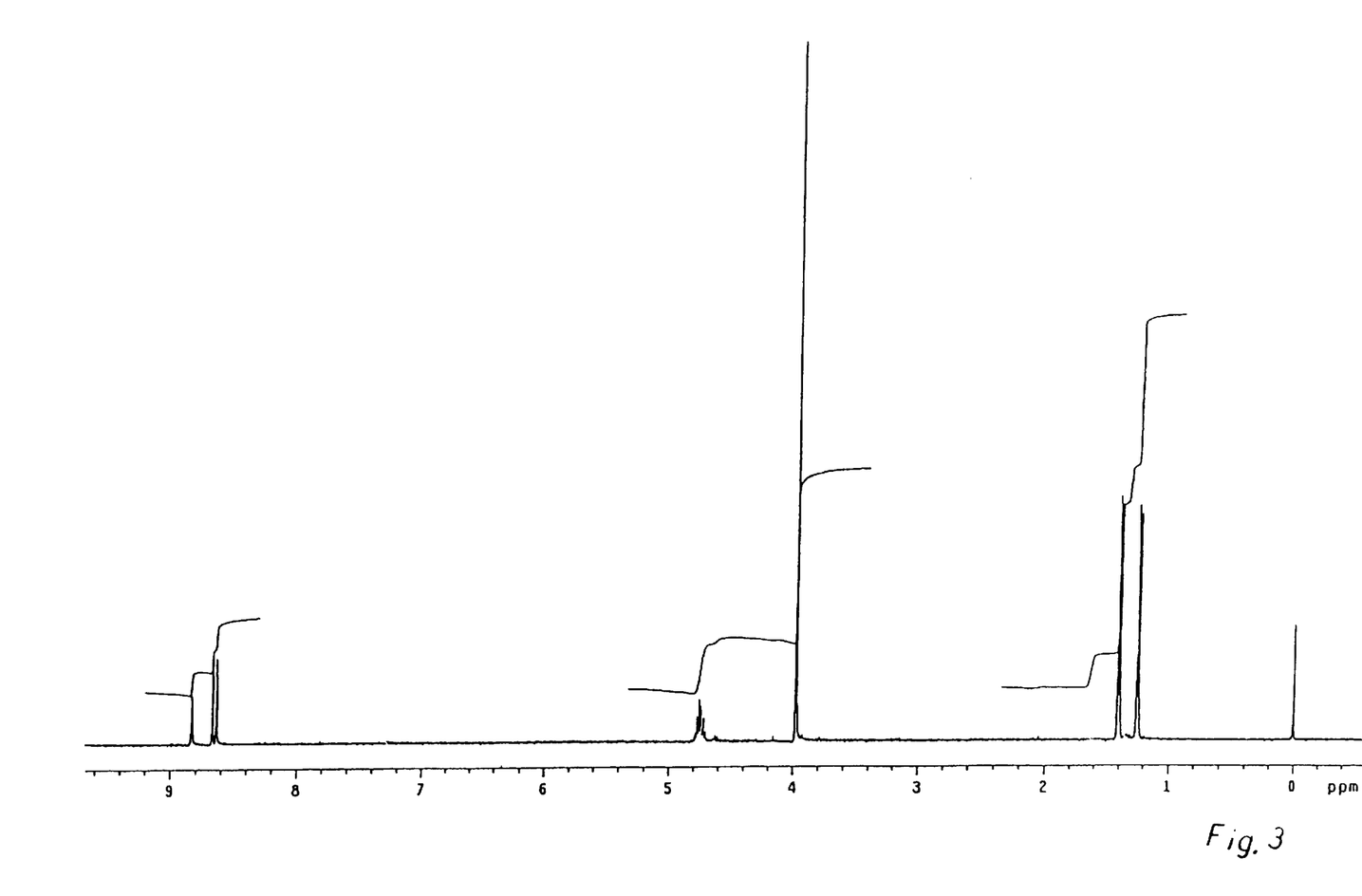
FIG. 3 is a $^1$H-NMR chart of di-i-propyl 3,5-dimethoxycarbonylphenylphosphonate obtained in Example 3.
Figure 4:
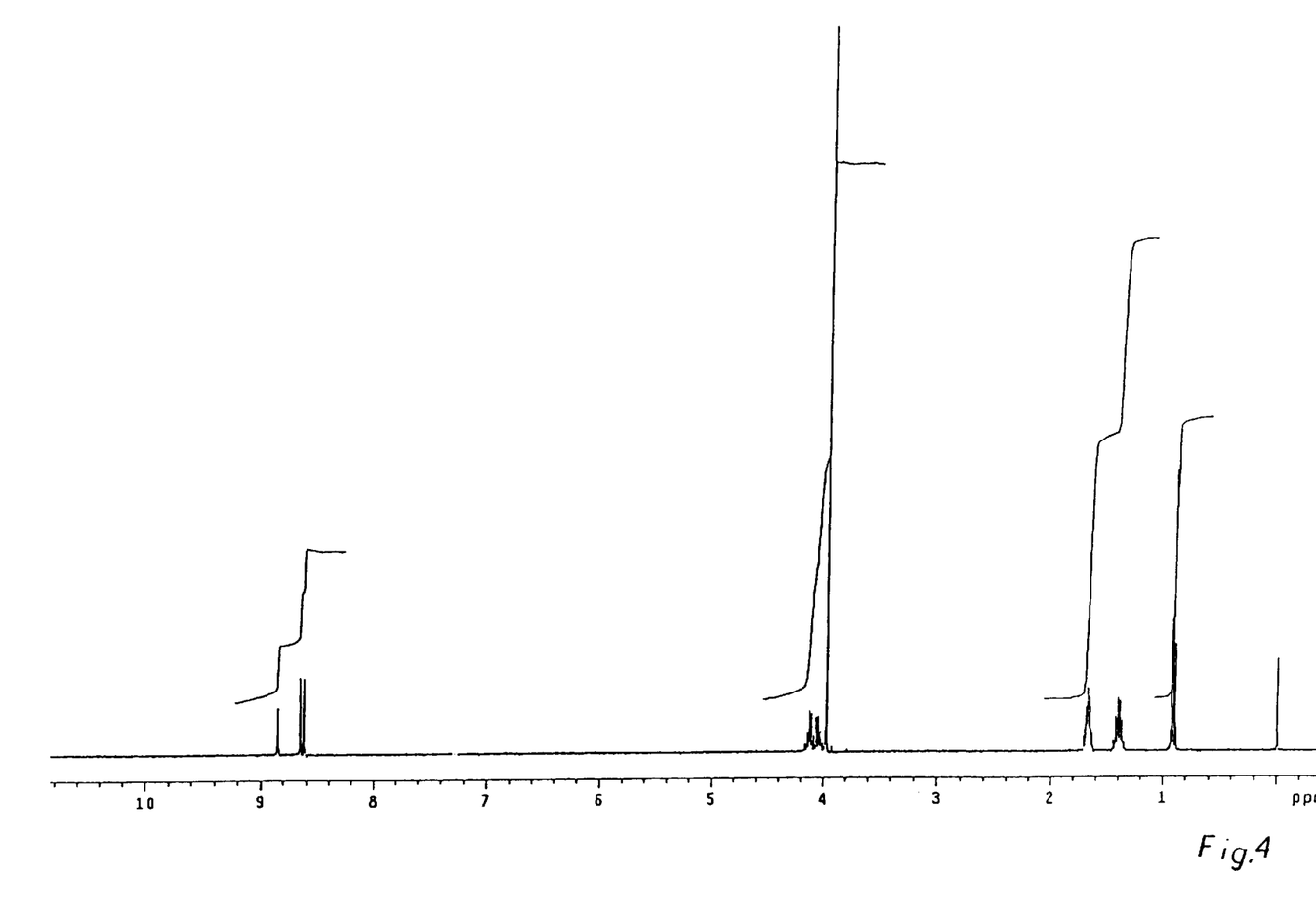
FIG. 4 is a $^1$H-NMR chart of di-n-butyl 3,5-dimethoxycarbonylphenylphosphonate obtained in Example 4.
Figure 5:
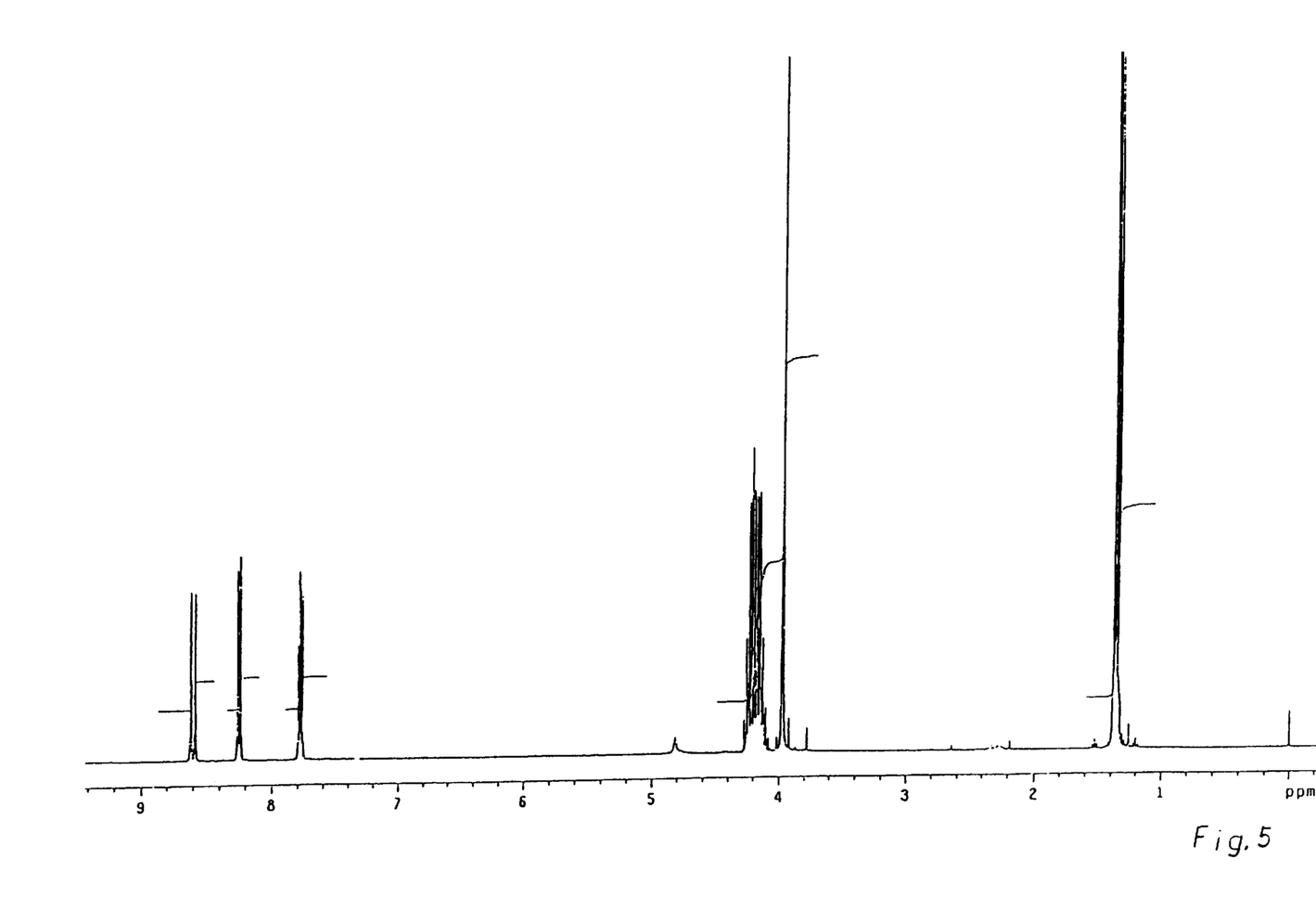
FIG. 5 is a $^1$H-NMR chart of diethyl 2,5-dimethoxycarbonylphenylphosphonate obtained in Example 5.
Figure 6:
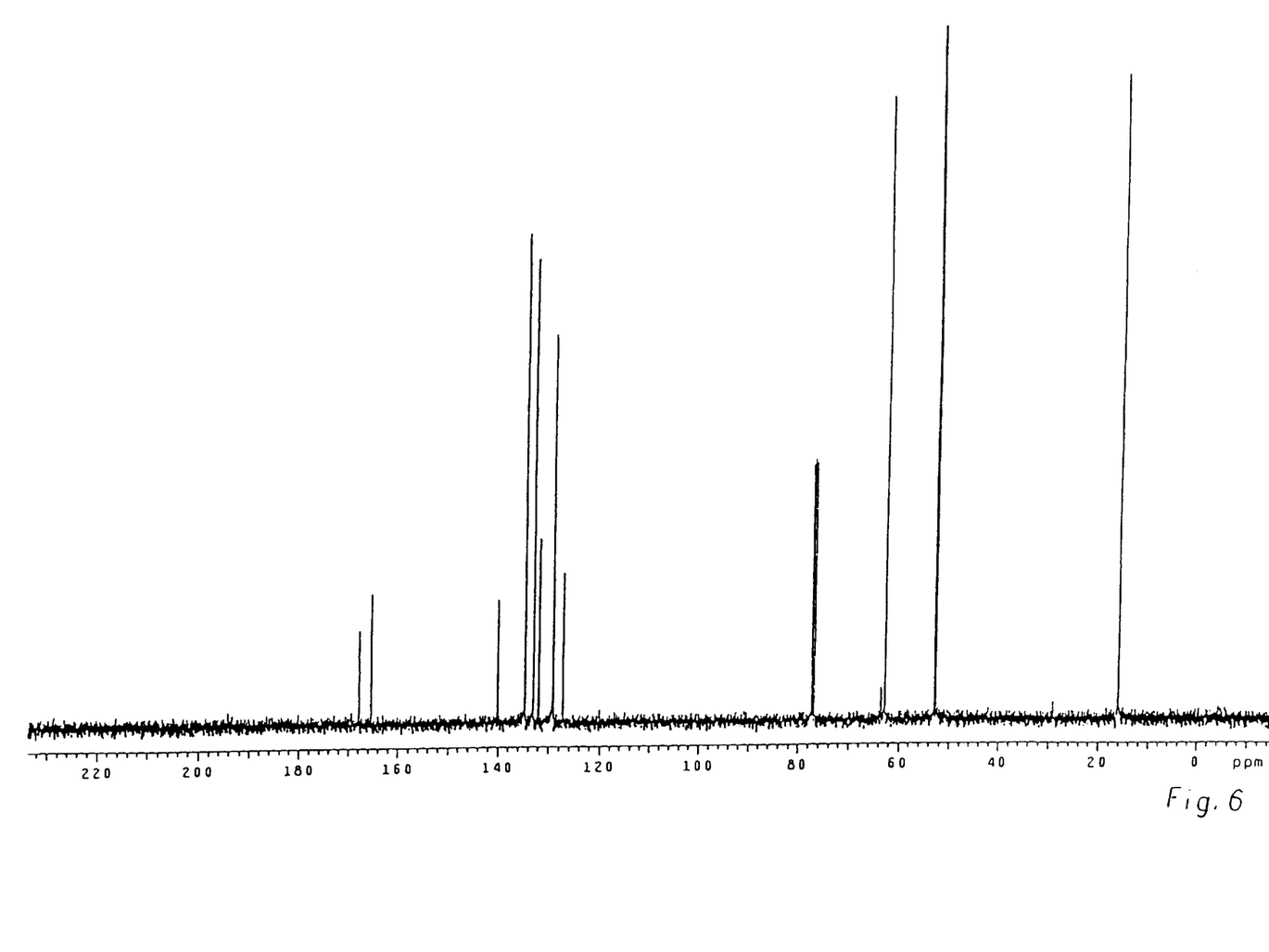
FIG. 6 is a $^{13}$C-NMR chart of diethyl 2,5-dimethoxycarbonylphenylphosphonate obtained in Example 5.
Figure 7:
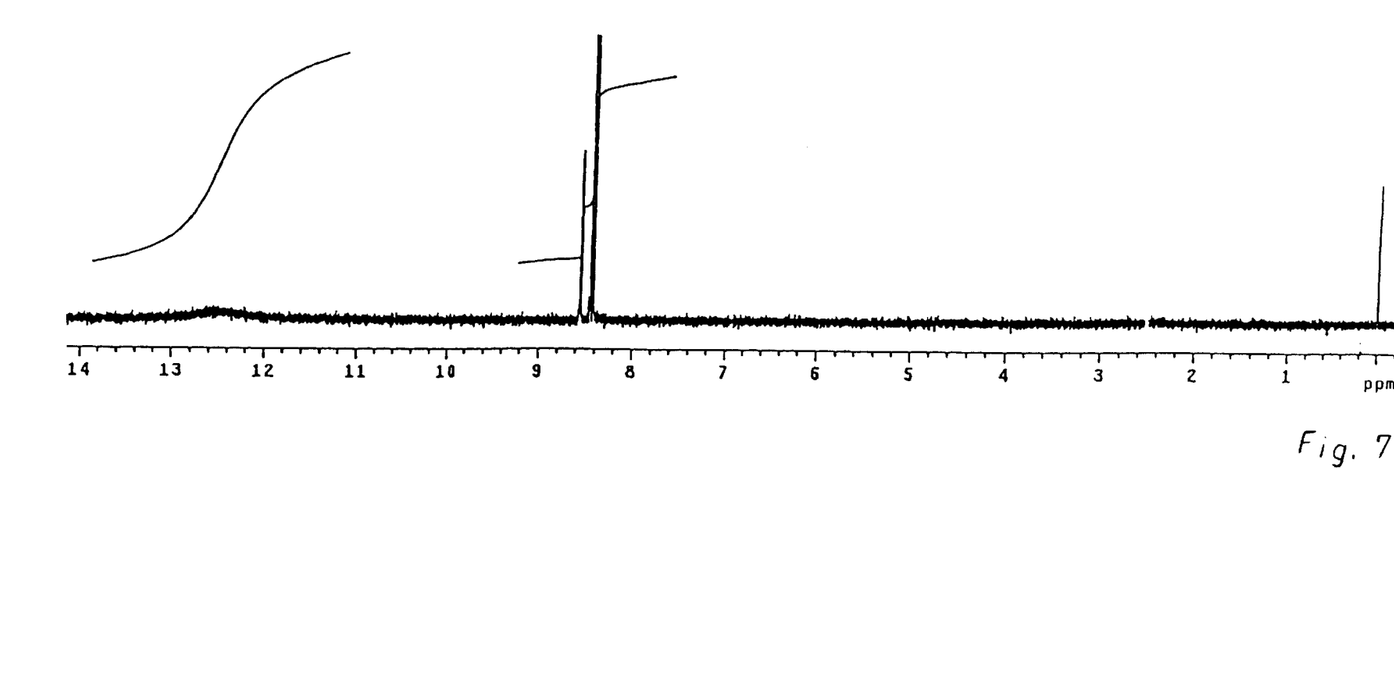
FIG. 7 is $^1$H-NMR chart of 3,5-dicarbonylphenylphosphonicacid obtained in Example 20.

The production process of the present invention will be described in detail.

The process for producing a dialkyl dialkoxycarbonylphenylphosphonate obtained by an Arbuzov reaction is first described hereinunder.

The dialkoxycarbonylphenyl halide usable in the production process of the present invention is represented by the following general formula (II):

wherein $R^4$ and $R^5$ are each selected from the group consisting of alkoxycarbonyl groups having 1 to 10 carbon atoms, X is a halogeno group, and $R^4$, $R^5$ and X are substituted at arbitrarily selected different positions on a benzene ring. Illustrative examples of the dialkoxycarbonylphenyl halide include dimethyl 5-chloroisophthalate, dimethyl 5-bromoisophthalate, dimethyl 5-iodoisophthalate, diethyl 5-chloroisophthalate, diethyl 5-bromoisophthalate, diethyl 5-iodoisophthalate, di-n-propyl 5-bromoisophthalate, di-i-propyl 5-bromoisophthalate, di-n-butyl 5-bromoisophthalate, di-s-butyl 5-bromoisophthalate, di-t-butyl 5-bromoisophthalate, di-n-pentyl 5-bromoisophthalate, di-t-pentyl 5-bromoisophthalate, di-n-hexyl 5-bromoisophthalate, di-n-hexyl 5-bromoisophthalate, di-n-heptyl 5-bromoisophthalate, di-n-octyl 5-bromoisophthalate, di-n-nonyl 5-bromoisophthalate, dimethyl 2-chloroterephthalate, dimethyl 2-bromoterephthalate, dimethyl 2-iodoterephthalate, diethyl 2-chloroterephthalate, diethyl 2-bromoterephthalate, diethyl 2-iodoterephthalate, di-n-propyl 2-bromoterephthalate, di-i-propyl 2-bromoterephthalate, di-n-butyl 2-bromoterephthalate, di-s-butyl 2-bromoterephthalate, di-t-butyl 2-bromoterephthalate, di-n-pentyl 2-bromoterephthalate, di-t-pentyl 2-bromoterephthalate, di-n-hexyl 2-bromoterephthalate, di-n-hexyl 2-bromoterephthalate, di-n-heptyl 2-bromoterephthalate, di-n-octyl 2-bromoterephthalate, di-n-nonyl 2-bromoterephthalate, dimethyl 3-bromophthalate, diethyl 3-bromophthalate, di-n-propyl 3-bromophthalate, di-i-propyl 3-bromophthalate, di-n-butyl 3-bromophthalate, di-s-butyl 3-bromophthalate, di-t-butyl 3-bromophthalate, dimethyl 4-bromophthalate, diethyl 4-bromophthalate, di-n-propyl 4-bromophthalate, di-i-propyl 4-bromophthalate, di-n-butyl 4-bromophthalate, di-s-butyl 4-bromophthalate, di-t-butyl 4-bromophthalate and the like. When they are compared with one another in terms of reactivity, iodides have higher reactivity than bromides which have higher reactivity than chlorides. Iodides have the highest reaction rate. From a view point of the production costs of halides, there are a few preferred processes for halogenating dialkyl phthalates. Iodides are more expensive than bromides which are more expensive than chlorides. From viewpoints of reactivity and costs which run counter to each other, bromides are preferred and dialkoxycarbonylphenyl bromide is particularly preferred.

The trialkyl phosphite usable in the production process of the present invention is represented by the following general formula (III):

$$(R^6O)_3P \qquad (III)$$

wherein $R^6$ is selected from the group consisting of alkyl groups having 1 to 10 carbon atoms.

Illustrative examples of the trialkyl phosphite include trimethyl phosphite, triethyl phosphite, tri-n-propyl phosphite, tri-i-propyl phosphite, tri-n-butyl phosphite, tri-s-butyl phosphite, tri-t-butyl phosphite, tri-n-pentyl phosphite, tri-i-pentyl phosphite, tri-t-pentyl phosphite, tri-n-hexyl phosphite, tri-n-heptyl phosphite, tri-n-octyl phosphite, tri-n-nonyl phosphite, tri-n-decyl phosphite and the like.

Out of these, trimethyl phosphite has a boiling point of 120° C. or lower which is lower than other phosphorous acid compounds. Therefore, as it cannot be heated up to a temperature of 120° C. which is required to carry out a reaction at normal pressure, the reaction must be carried out under pressure. Other phosphorous acid compounds can be heated up to a temperature of 120° C. at normal pressure and a dialkyl dialkoxycarbonylphenylphosphonate can be obtained in high yield.

The catalyst usable in the production process of the present invention is a catalyst comprising an element of group VIII of the periodic table. Preferred examples of the catalyst include palladium catalysts, nickel catalysts and cobalt catalysts which comprise elements of group VIII of the periodic table. Palladium catalysts and nickel catalyst are more preferred and palladium catalysts are the most preferred. Copper catalysts may be used but inferior to catalysts comprising elements of group VIII of the periodic table in catalytic performance.

A preferred catalyst can be selected according to the type of the dialkoxycarbonylphenyl halide. When the raw material was dialkyl 5-halogenoisophthalate, palladium catalysts were almost equivalent to nickel catalysts which were superior to cobalt catalysts in the yield of the dialkyl dialkoxycarbonylphenylphosphonate of interest. It has been found that palladium catalysts and nickel catalysts are preferred. When the raw material was dialkyl 2-halogenoterephthalate, palladium catalysts were superior to nickel catalysts which were superior to cobalt catalysts in the yield of the dialkyl dialkoxycarbonylphenylphosphonate of interest. It has been found that palladium catalysts are preferred.

The elements of these catalysts are preferably metals, metal oxides, inorganic acid salts, organic acid salts, O-valent complexes, alloys thereof and supported catalysts thereof.

Specific example of palladium catalysts include metal catalysts such as palladium black; inorganic acid salt catalysts such as palladium chloride, palladium bromide, palladium iodide, palladium nitrate and palladium sulfate; organic acid salt catalysts such as palladium formate and palladium acetate; O-valent complex catalysts such as tetrakistriphenylphosphine palladium and palladium acetyl acetonate; supported catalysts, particularly supported metal catalysts such as activated carbon supported palladium catalyst, alumina supported palladium catalyst, zeolite supported palladium catalyst, diatomaceous earth supported palladium catalyst and ion exchange resin supported palladium catalyst; and the like.

Specific example of nickel catalysts include metal catalysts such as nickel powder, Raney nickel and nickel-aluminum alloy; inorganic acid salt catalysts such as nickel chloride, nickel bromide, nickel iodide, nickel nitrate and nickel sulfate; organic acid salt catalysts such as nickel formate and nickel acetate; O-valent complex catalysts such as tetrakistriphenylphosphine nickel and nickel acetyl acetonate; supported catalysts, particularly supported metal catalysts such as activated carbon supported nickel catalyst, alumina supported nickel catalyst, zeolite supported nickel catalyst, diatomaceous earth supported nickel catalyst and ion exchange resin supported nickel catalyst; and the like.

Cobalt catalysts include inorganic acid salt catalysts such as cobalt chloride, cobalt bromide, cobalt iodide, cobalt nitrate and cobalt sulfate; organic acid salt catalysts such as cobalt formate and cobalt acetate; O-valent complex catalysts such as cobalt acetyl acetonate; supported catalysts, particularly supported metal catalysts such as alumina supported cobalt catalyst and diatomaceous earth supported cobalt catalyst; and the like.

Supported catalysts produced by known methods have not been used as a catalyst in the Arbuzov reaction. The inventors of the present invention have studied supported catalysts (particularly supported metal catalysts) for the purpose of recover and reuse of a catalyst which are important for practical use and have found a supported catalyst from which a dialkyl dialkoxycarbonylphenylphosphonate is obtained in high yield like an inorganic salt catalyst which has been used as a catalyst in the Arbuzov reaction. Further, they have confirmed that the supported catalyst can be reused.

Carriers for the supported catalysts include general diatomaceous earth, bentonite, bauxite, alundum, corundum, pumice, brick, celite, acid clay, activated carbon, magnesia, alumina, silica gel, silica alumina, titania, chromina, zinc oxide, thoria, calcium carbonate, barium sulfate, magnesium carbonate, silicon carbide, zeolite, molecular sieve, ion exchange resins and the like. Out of these, activated carbon, alumina, silica gel, silica alumina and zeolite are preferred. Alumina, silica gel, silica alumina and zeolite are more preferred. Alumina is the most preferred.

The amount of the catalyst used in the production process of the present invention is preferably 0.01 to 30 mol %, more preferably 0.2 to 20 mol %, the most preferably 0.5 to 5 mol %, in terms of atoms of the element of group VIII of the periodic table of the catalyst based on 1 mole of the dialkoxycarbonylphenyl halide as a raw material.

In the Arbuzov reaction, the catalyst has been used in an amount of 10 mol % in terms of the atoms of the element of group VIII of the periodic table or copper element of the catalyst based on 1 mole of the halide as a raw material in most cases. The present invention has succeeded in reducing the amount of a catalyst used to 1 mol % or less in terms of the atoms of an element of group VIII of the periodic table of the catalyst based on 1 mole of the halide by using a supported metal catalyst. Particularly, when a 5% palladium catalyst supported by alumina is used in an amount of 0.5 mol % in terms of the atoms of the palladium component of the catalyst based on 1 mole of the halide, a fixed quantity of a dialkyl dialkoxycarbonylphenylphosphonate can be obtained. Further, it has been confirmed that even when a catalyst is used in an amount of 0.2 mol % in terms of the atoms of the palladium component of the catalyst based on 1 mole of the halide, a raw material conversion of 50% or more is obtained.

As described above, in the present invention, as a supported metal catalyst, particularly by using an alumina supported palladium catalyst, a reduction in the amount of the catalyst used and the reuse of the catalyst are made possible and an industrially advantageous process for producing a dialkyl dialkoxycarbonylphenylphosphonate can be provided.

Although the Arbuzov reaction can be carried out without a solvent in the production process of the present invention, it has been found that use of a solvent is effective in promoting the proceeding of the reaction when a reaction substrate, a raw material, is solid, and suppressing the production of a by-product to improve the selectivity of the dialkyl dialkoxycarbonylphenylphosphonate.

Any solvents can be used if they do not take part in the Arbuzov reaction directly. Preferred solvents are aromatic hydrocarbons and ethers.

Illustrative examples of the solvent include toluene, xylene, ethyl benzene, cumene, t-butylbenzene, di-i-propylbenzene, 1,2-dimethoxyethane, 1,2-diethoxyethane, 2-methoxyethane, diethylene glycol dimethyl ether, diethylene glycol diethyl ether, triethylene glycol dimethyl ether, 1,4-dioxane, 1,3-dioxane and the like.

Out of these, solvents having a boiling point of 150° C. or lower can be used under pressure and solvents having a boiling point of 150° C. or higher can be used at normal pressure. As a matter of course, solvents having a boiling point of 150° C. or higher can be used under pressure. Out of these, preferred solvents which can be used at normal pressure include cumene, t-butylbenzene, di-i-propylbenzene, diethylene glycol dimethyl ether, diethylene glycol diethyl ether, triethylene glycol dimethyl ether and the like.

The amount of the solvent used is preferably 0.1 to 10 parts by weight, more preferably 0.5 to 5 parts by weight, based on 1 part by weight of the dialkoxycarbonylphenyl halide as a raw material.

In the production process of the present invention, the Arbuzov reaction is carried out by heating. Since the reaction proceeds too slow at a temperature of 120° C. or lower, the reaction temperature must be 120° C. or higher. That is, the reaction temperature is preferably 120° to 250° C., more preferably 140° to 220° C., the most preferably 155° to 220° C.

The reaction time of the Arbuzov reaction in the production process of the present invention is such that the proceeding of the reaction can be tracked by the analysis of the reaction solution by gas chromatography or high-speed liquid chromatography. Therefore, the reaction end point of interest can be found by analysis such as gas chromatography or high-speed liquid chromatography.

The reaction time is generally 1 to 20 hours, preferably 1 to 10 hours from an industrial point of view.

The Arbuzov reaction in the production process of the present invention can be carried out at normal pressure or under pressure and in a batch or continuous manner.

As for a treatment after the Arbuzov reaction, the solvent, excessive or unreacted dialkoxycarbonylphenyl halide and excessive or unreacted trialkyl phosphite are recovered by distillation and then, a dialkyl dialkoxycarbonylphenylphosphonate as the reaction product is purified and isolated by distillation, recrystallization, column chromatography and the like in accordance with a commonly used method.

A description is subsequently given of a process for producing a dicarboxyphenylphosphonic acid which is obtained by hydrolyzing the dialkyl dialkoxycarbonylphenylphosphonate.

A hydrolytic reaction requires the presence of an acid or base.

Illustrative examples of the acid include inorganic acids such as hydrofluoric acid, hydrochloric acid, hydrobromic acid, sulfuric acid and phosphoric acid; and organic acids such as methanesulfonic acid, trifluoromethanesulfonic acid and trifluoroacetic acid. Out of these, hydrochloric acid and hydrobromic acid are particularly preferred.

Illustrative examples of the base include inorganic bases such as sodium hydroxide, potassium hydroxide, magnesium hydroxide, calcium hydroxide and barium hydroxide; and organic bases such as 1,5-diazabicyclo[4.3.0]non-5-en, 1,4-diazabicyclo[2.2.2]octane, 1,8-diazabicyclo[5.4.0]undec-7-en, and triethylamine. Out of these, sodium hydroxide and potassium hydroxide are particularly preferred.

The amount of an acid or base used is 2 to 40 equivalents, preferably 4 to 20 equivalents, based on the dialkyl dialkoxycarbonylphenylphosphonate as a raw material.

A solvent can be used in the hydrolytic reaction. The solvent is water and an organic solvent. Illustrative examples of the organic solvent include ethers such as 1,2-dimethoxyethane and 1,4-dioxane; alcohols such as ethanol and n-butanol; and aliphatic hydrocarbon halides such as 1,2-dichloroethane and 1,2,3-trichloropropane. These organic solvents may be used alone or in admixture of two or more.

The amount of the solvent used in the hydrolytic reaction is 0 to 100 times, preferably 0 to 20 times the weight of the dialkyl dialkoxycarbonylphenylphosphonate as a raw material.

The hydrolytic reaction may be carried out at a temperature near the boiling point of the solvent but may be carried out in a hermetically sealed device under pressure. Therefore, the reaction temperature is 0° to 200° C., preferably 50° to 150° C. The reaction time is 1 to 24 hours, preferably 1 to 10 hours.

The hydrolytic reaction can be carried out at normal pressure or under pressure and in a batch or continuous manner.

As for a treatment after the hydrolytic reaction, when the treatment is carried out in the presence of an acid, a reacted solution or concentrated solution thereof is cooled to deposit crystals. The deposited crystals are filtrated and dried to obtain the dicarboxyphenylphosphonic acid of interest. When the treatment is carried out in the presence of a base, an acid more than the equivalent of the base is added and then a reacted solution or concentrated solution thereof is treated to obtain the dicarboxyphenylphosphonic acid of interest as in the case where the treatment is carried out in the presence of an acid.

When the dicarboxyphenylphosphonic acid must be purified, its purity can be improved by a recrystallization method using a solvent such as methanol or dioxane.

EXAMPLE

The following examples are provided for the purpose of further illustrating the present invention but are in no way to be taken as limiting.

Experimental and analytical methods employed in the following examples are described below.
[silica gel chromatography (SGCG)]

In Examples 1 to 4, silica gel chromatography (developing solution: a mixture solvent of heptane and ethyl acetate) was used to purify the dialkyl dialkoxycarbonylphenylphosphonate as a reaction product.
[gas chromatography (GC)]

In Examples 1 to 5, gas chromatography was used to confirm the purity of the dialkyl dialkoxycarbonylphenylphosphonate as a reaction product. In Examples 6 to 17, gas chromatography was used to analyze the reaction product collected into an EDC extract as a mixture. The relative area ratio (%) of the reaction product was obtained by the analysis of data obtained by the gas chromatography. The relative area ratio (%) of the dialkoxycarbonylphenyl halide as a raw material was also obtained in the same manner.
conditions of gas chromatography:
device: Shimadzu GC-17A, column: capillary column CBP1-W25-100 (25 mm×0.53 mm $\phi$×1 $\mu$m), column temperature: controlled using a temperature elevation program and 260° C. was obtained by elevating temperature from 100° C. at a rate of 10° C./min., injection temperature: 290° C., temperature of detector: 290° C., carrier gas: helium, detection method:
FID method
[high-speed liquid chromatography (HPLC)]

In Examples 5 and 19, the reaction product was analyzed by high-speed liquid chromatography as a mixture. The relative area ratio (%) of the reaction product was obtained by the analysis of data obtained by the high-speed liquid chromatography.
conditions of high-speed liquid chromatography:
device: Hitachi L-400, column: Pack ODS-AM (4.6 mm φ×250 mm) of YMC Co., oven temperature: 40.0° C., carrier solvent: mixture solvent of acetonitrile and water (2/1 (V/V)), detection method: UV detection method (254 nm)

In Examples 21 to 28, the hydrolytic reaction product was analyzed by high-speed liquid chromatography as a mixture. The relative area ratio (%) of the reaction product was. obtained by the analysis of data obtained by the high-speed liquid chromatography.
conditions of high-speed liquid chromatography:
device: Shimadzu LC-10A, column: Pack ODS-AM (4.6 mm φ×250 mm) of YMC Co., oven temperature: 40.0° C., carrier solvent: mixture solvent of water, acetic acid and ammonium acetate (150/2/5.5 (V/V/V)), detection method: UV detection method (240 nm)
[mass spectrometry (MASS)]

In Examples 1, 4 and 20, an FAB method was used to identify the reaction product and in Examples 2, 3, 5 and 32, an FD method was used to identify the reaction product.

The LX-1000 of JEOL Ltd. was used as a device for carrying out the FAB method. The SX-102 of JEOL Ltd. was used as a device for carrying out the FD method.
[proton nuclear magnetic resonance method ($^1$H-NMR)]

In Examples 1 to 5, a proton nuclear magnetic resonance method ($^1$H-NMR) was used to identify the reaction product.
conditions of proton nuclear magnetic resonance method ($^1$H-NMR):device: INOVA400 of VARIAN Corp., measurement solvent: $CDCl_3$ or $D_6$-DMSO, reference substance: tetramethylsilane (TMS)
[$^{13}$C nuclear magnetic resonance method ($^{13}$C-NMR)]

In Example 5, a 13C nuclear magnetic resonance method ($^{13}$C-NMR) was used to identify the reaction product. conditions of $^{13}$C nuclear magnetic resonance method ($^{13}$C-NMR): device: INOVA400 of VARIAN Corp., measurement solvent: $CDCl_3$, reference substance: $CDCl_3$ (6:77.1 ppm)
[elemental analysis]

In Example 32, carbon, nitrogen and hydrogen were measured by CHN elemental analysis. Phosphorus was measured by vanadomolybdophosphate absorption photometry. conditions of CHN elemental analysis: device: 2400CHN of Perkin-Elmer Corp.
[infrared absorption spectrophotometry]

In Example 32, the functional group of the hydrolytic reaction product was determined by infrared absorption spectrophotometry.
conditions of infrared absorption spectrophotometry:
device: FT-210 of Horiba, Ltd.
[thermal analysis (DSC)]

In Examples 20 and 32, the melting point was measured by DSC.
DSC measurement conditions: device: Thermoplus of Rigaku Corp.

Examples of the present invention are described hereinunder.

Example 1

A magnetic stirrer was placed in a stainless steel autoclave having an inner volume of 50 ml, and 1.4 g (5 mmols) of dimethyl 5-bromoisophthalate, 2.5 g (20 mmols) of trimethyl phosphite and 65 mg (0.5 mmol in terms of the atoms of nickel component) of nickel chloride were added to the autoclave and heated at a reaction temperature of 180° C. for 7 hours under agitation to carry out a reaction. The pressure inside the autoclave was 4 atm. during the reaction.

After completion of the reaction, water and 1,2-dichloroethane (EDC) were added to the reaction mixture obtained by cooling and the reaction product was extracted into an EDC phase. The EDC phase was separated, washed with water, and concentrated at a reduced pressure to obtain 1.3 g of an oily substance.

When this oily substance was purified by silica gel chromatography, 0.98 g of crystals (yield of 65%) was obtained. It was confirmed by gas chromatography that the crystals were composed of a single component.
(identification results of crystals)
melting point (° C.) : 88 to 89
MASS (FAB method) m/e (%): 303 ($M^+$, 100), 289 (6), 271 (16), 65 (23)
$^1$H-NMR (400 MHz, solvent: $CD_3Cl$, reference substance: TMS)δ ppm: 3.80 (s, 3H), 3.83 (s, 3H), 3.98 (s, 6H), 8.62 (d, J=1.6 Hz, 1H), 8.65 (d, J=1.6 Hz, 1H), 8.87 (t, J=1.6 Hz, 1H)

It was confirmed from the above results that the crystals were composed of dimethyl 3,5-dimethoxycarbonylphenylphosphonate of interest.

Example 2

A magnetic stirrer was placed in a glass reaction flask equipped with a cooling tube and having an inner volume of 50 ml, and 1.4 g (5 mmols) of dimethyl 5-bromoisophthalate, 1.7 g (10 mmols) of triethyl phosphite and 65 mg (0.5 mmol in terms of the atoms of nickel component) of nickel chloride were added to the flask and heated at a reaction temperature of 150° to 155° C. for 4 hours under agitation to carry out a reaction.

After completion of the reaction, water and 1,2-dichloroethane (EDC) were added to the reaction mixture obtained by cooling and the reaction product was extracted into an EDC phase. The EDC phase was separated, washed with water and concentrated at a reduced pressure to obtain 1.9 g of an oily substance.

When this oily substance was purified by silica gel chromatography, 1.4 g (yield of 85%) of crystals were obtained. It was confirmed by gas chromatography that the crystals were composed of a single component.
(identification results of crystals)
melting point (° C): 45 to 46
MASS (FD method) m/e (%): 330 ($M^+$, 100) $^1$H-NMR (400 MHz, solvent: $CD_3Cl$, reference substance: TMS)δppm: 1.35 (t, J=6.96 Hz, 6H), 3.97 (t, J=2.75 Hz, 3H), 3.98 (t, J=2.75 Hz, 3H), 4.10 to 4.21 (m, 4H), 8.63 (s, 1H), 8.66 (s, 1H), 8.85 (s, 1H)

It was confirmed from the above results that the crystals were composed of diethyl 3,5-dimethoxycarbonylphenylphosphonate of interest.

Example 3

A magnetic stirrer was placed in a glass reaction flask equipped with a cooling tube and having an inner volume of 50 ml, and 1.4 g (5 mmols) of dimethyl 5-bromoisophthalate, 2.1 g (10 mmols) of tri-i-propyl phosphite and 65 mg (0.5 mmol in terms of the atoms of nickel component) of nickel chloride were added to the flask and heated at a reaction temperature of 150° to 155° C. for 4 hours under agitation to carry out a reaction.

After completion of the reaction, water and 1,2-dichloroethane (EDC) were added to the reaction mixture obtained by cooling and the reaction product was extracted into an EDC phase. The EDC phase was separated, washed with water and concentrated at a reduced pressure to obtain 1.7 g of an oily substance.

When this oily substance was purified by silica gel chromatography, 1.2 g (yield of 67%) of crystals were obtained. It was confirmed by gas chromatography that the crystals were composed of a single component.
(identification results of crystals)
melting point (° C.): 109 to 110
MASS (FD method) m/e (%): 359 (M$^+$, 100)
$^1$H-NMR (400 MHz, solvent: CD$_3$Cl, reference substance: TMS)δ ppm : 1.24 (d, J=6.22 Hz, 6H), 1.40 (d, J=6.22 Hz, 6H), 3.97 (t, J=4.0 Hz, 6H), 4.72 to 4.77 (m, 2H), 8.63 (d, J=1.65 Hz, 1H), 8.67 (d, J=1.65 Hz, 1H), 8.83 (s, 1H)

It was confirmed from the above results that the crystals were composed of di-i-propyl 3,5-dimethoxycarbonylphenylphosphonate of interest.

Example 4

A magnetic stirrer was placed in a glass reaction flask equipped with a cooling tube and having an inner volume of 50 ml and 1.4 g (5 mmols) of dimethyl 5-bromoisophthalate, 2.4 g (10 mmols) of tri-n-butyl phosphite and 65 mg (0.5 mmol in terms of the atoms of nickel component) of nickel chloride were added to the flask and heated at a reaction temperature of 150° to 155° C. for 4 hours under agitation to carry out a reaction.

After completion of the reaction, water and 1,2-dichloroethane (EDC) were added to the reaction mixture obtained by cooling and the reaction product was extracted into an EDC phase. The EDC phase was separated, washed with water and concentrated at a reduced pressure to obtain 2.3 g of an oily substance.

When this oily substance was purified by silica gel chromatography, 1.6 g (yield of 83%) of crystals were obtained. It was confirmed by gas chromatography that the crystals were composed of a single component.
(identification results of crystals)
melting point ( C): 66 to 67
MASS (FD method) m/e (%): 387 (M$^+$, 23), 355 (10), 331 (5), 275 (100)
$^1$H-NMR (400 MHz, solvent: CD$_3$Cl, reference substance: TMS)δ ppm :0.92 (t, J=7.3 Hz, 6H), 1.35 to 1.43 (m, 4H), 1.64 to 1.71 (m, 4H), 3.98 (s, 6H), 4.01 to 4.15 (m, 4H), 8.62 (s, 1H), 8.66 (s, 1H), 8.85 (s, 1H)

It was confirmed from the above results that the crystals were composed of di-n-butyl 3,5-dimethoxycarbonylphenylphosphonate of interest.

Example 5

A magnetic stirrer was placed in a glass reaction flask equipped with a cooling tube and having an inner volume of 50 ml, and 7.8 g (28 mmols) of dimethyl 2-bromoterephthalate, 19.0 g (112 mmols) of triethyl phosphite and 0.51 g (2.8 mmols in terms of the atoms of palladium component) of palladium chloride were added to the flask and heated at a reaction temperature of 150° C. for 3 hours under agitation to carry out a reaction.

After completion of the reaction, water and 1,2-dichloroethane (EDC) were added to the reaction mixture obtained by cooling and the reaction product was extracted into an EDC phase. The EDC phase was separated, washed with water and dried with anhydrous magnesium sulfate. When the dried EDC extract was concentrated at a reduced pressure, 9.0 g (yield of 94%) of an achromatic oily substance was obtained.

This oily substance was analyzed by high-speed liquid chromatography. The relative area ratio (%) of the reaction product was 97% according to the analysis of data obtained by the high-speed liquid chromatography.
(identification results of oily substance)
MASS (FD method) m/e (%): 330 (M$^+$, 100)
$^1$H-NMR (400 MHz, solvent: CD$_3$Cl, reference substance: TMS)δ ppm 1.37 (t, J=7.14 Hz, 6H), 3.97 (s, 6H), 4.10 to 4.26 (m, 4H), 7.78 (dd, J=8.06 Hz, 4.8 Hz, 1H), 8.25 (dt, J=8.06 Hz, 1.5 Hz, 1H), 8.60 (dd, J=14.3 Hz, 1.6H, 1H)
$^{13}$C-NMR (100 MHz, solvent: CD$_3$Cl, reference substance: CD$_3$Cl) δ ppm: 16,2, 16.3, 52.6, 52.9, 62.8, 127.2, 129.1, 131.9, 133.0, 134.6, 140.0, 165.4, 167.8)

It was confirmed from the above results that the crystals were composed of diethyl 2,5-dimethoxycarbonylphenylphosphonate of interest.

Examples 6 to 12

A magnetic stirrer was placed in a glass reaction flask equipped with a cooling tube and having an inner volume of 50 ml, and 0.55 g (2 mmols) of dimethyl 5-bromoisophthalate, 0.66 g (4 mmols) of triethyl phosphite and catalysts (nickel chloride (NiCl$_2$), palladium chloride (PdCl$_2$), alumina supported 5% palladium catalyst (5% Pd/Al$_2$O$_3$), cobalt bromide (CoBr$_2$), copper bromide (CuBr$_2$) and the like] were added to the flask and heated at a reaction temperature of 155° to 165° C. for a predetermined time duration under agitation to carry out a reaction.

After completion of the reaction, water and 1,2-dichloroethane (EDC) were added to the reaction mixture obtained by cooling and the reaction product was extracted into an EDC phase. The EDC phase was separated and washed with water to obtain an EDC extract.

This EDC extract was analyzed by gas chromatography (GC). The GC relative area ratio (%) of diethyl 3,5-thoxycarbonylphenylphosphonate (DDPP) which was the reaction product was obtained by the analysis of data obtained by the gas chromatography. The GC relative area ratio (%) of dimethyl 5-bromoisophthalate (DBIP) as the raw material was also obtained in the same manner. The conditions are shown in Table 1 and the results are shown in Table 2.

TABLE 1

| | catalyst | | reaction time |
|---|---|---|---|
| Example | type | quantity (mg/mol %) | (h) |
| 6 | NiCl$_2$ | 11/4 | 1 |
| 7 | NiCl$_2$ | 2.6/1 | 2 |
| 8 | PdCl$_2$ | 53/10 | 2 |
| 9 | 5% Pd/Al$_2$O$_3$ | 42/1 | 1 |
| 10 | 5% Pd/Al$_2$O$_3$ | 8/0.2 | 2 |
| 11 | CoBr$_2$ | 66/15 | 2 |
| 12 | CuBr$_2$ | 45/10 | 2 |

(Note)
As for the quantity of catalyst in Table 1, the weight of the catalyst is expressed in mg. The quantity of the element of group VIII of the periodic table or copper element of the catalyst based on 1 mole of the dialkoxycarbonylphenyl halide is calculated in terms of atoms and expressed in mol %.

TABLE 2

| | GC relative area ratio | |
|---|---|---|
| Example | DDPP (%) | DBIP (%) |
| 6 | 95 | 3 |
| 7 | 91 | 6 |
| 8 | 94 | 4 |
| 9 | 94 | 2 |
| 10 | 51 | 48 |
| 11 | 14 | 57 |
| 12 | 7 | 83 |

Examples 13 and 16

A magnetic stirrer was placed in a glass reaction flask equipped with a cooling tube and having an inner volume of 50 ml, and 0.55 g (2 mmols) of dimethyl 5-bromoisophthalate, 0.66 g (4 mmols) of triethyl phosphite, solvents [cumene, diethylene glycol dimethyl ether (DGDE) and the like] and catalysts (nickel chloride ($NiCl_2$), activated carbon supported 5% palladium catalyst (5% Pd/C), alumina supported 5% palladium catalyst (5% $Pd/Al_2O_3$) and the like] were added to the flask and heated at a reaction temperature of 155° to 170° C. for a predetermined time duration under agitation to carry out a reaction.

After completion of the reaction, water and 1,2-dichloroethane (EDC) were added to the reaction mixture obtained by cooling and the reaction product was extracted into an EDC phase. The EDC phase was separated and washed with water to obtain an EDC extract.

This EDC extract was analyzed by gas chromatography (GC). The relative area ratio (%) of diethyl 3,5-dimethoxycarbonylphenylphosphonate (DDPP) which was the reaction product was obtained by the analysis of data obtained by the gas chromatography. The relative area ratio (%) of dimethyl 5-bromoisophthalate (DBIP) as the raw material was also obtained in the same manner. The conditions are shown in Table 3 and the results are shown in Table 4.

TABLE 3

| | catalyst | | solvent | | reaction |
|---|---|---|---|---|---|
| Example | type | quantity (mg/mol %) | type | quantity (g) | time (h) |
| 13 | $NiCl_2$ | 26/10 | cumene | 1.1 | 1 |
| 14 | 5% Pd/C | 210/5 | cumene | 1.1 | 1 |
| 15 | 5% $Pd/Al_2O_3$ | 210/5 | cumene | 1.1 | 1 |
| 16 | 5% $Pd/Al_2O_3$ | 21/0.5 | DGDE | 1.1 | 2 |

(Note)
As for the quantity of catalyst in Table 3, the weight of the catalyst is expressed in mg. The quantity of the element of group VIII of the periodic table of the catalyst based on 1 mole of the dialkoxycarbonylphenyl halide is calculated in terms of atoms and expressed in mol %.

TABLE 4

| | GC relative area ratio | |
|---|---|---|
| Example | DDPP (%) | DBIP (%) |
| 13 | 93 | 7 |
| 14 | 52 | 44 |
| 15 | 89 | 10 |
| 16 | 98 | 0 |

Example 17

A magnetic stirrer was placed in a glass reaction flask equipped with a cooling tube and having an inner volume of 50 ml, and 1.4 g (5 mmol) of dimethyl 5-bromoisophthalate, 1.7 g (10 mmol) of triethyl phosphite, 2.7 g of diethylene glycol dimethyl ether and 0.23 g (2 mmol in terms of the atoms of palladium component) of an alumina supported 5% palladium catalyst (5% $Pd/Al_2O_3$) were added to the flask and heated at a reaction temperature of 160° to 170° C. for 4 hours under agitation and the reflux of the solvent to carry out a reaction.

After completion of the reaction, the catalyst and the reaction mixture were cooled and separated from each other by filtration. Thereafter, the obtained reaction mixture was analyzed by gas chromatography. The relative area ratio (%) of diethyl 3,5-dimethoxycarbonylphenylphosphonate which was the reaction product was 91% according to the analysis of data obtained by the gas chromatography. The relative area ratio (%) of dimethyl 5-bromoisophthalate as the raw material was 7%.

The collected catalyst was washed with diethylene glycol dimethyl ether and placed in the glass reaction flask equipped with a cooling tube and having an inner volume of 50 ml together with the magnetic stirrer. Thereafter, 1.4 g (5 mmols) of dimethyl 5-bromoisophthalate, 1.7 g (10 mmols) triethyl phosphite and 2.7 g of diethylene glycol dimethyl ether were added to the flask and heated at a reaction temperature of 160° to 170° C. for 8 hours under agitation and the reflex of the solvent to carry out a reaction.

After completion of the reaction, the catalyst and the reaction mixture were cooled and separated from each other by filtration. Thereafter, the obtained reaction mixture was analyzed by gas chromatography. The relative area ratio (%) of diethyl 3,5-dimethoxycarbonylphenylphosphonate which was the reaction product was 82% according to the analysis of data obtained by the gas chromatography. The relative area ratio (%) of dimethyl 5-bromoisophthalate (DBIP) as the raw material was 14%.

Example 18

The reaction product was extracted into an EDC phase in the same manner as in Example 5 except that 0.47 g (10 mmols in terms of the atoms of nickel component) of nickel chloride was used as a catalyst in place of palladium chloride in Example 5.

The obtained EDC extract was analyzed by high-speed liquid chromatography. The relative area ratio (%) of diethyl 2,5-dimethoxycarbonylphenylphosphonate which was the reaction product was 28% according to the analysis of data obtained by the high-speed liquid chromatography.

Example 19

A magnetic stirrer was placed in a glass reaction flask equipped with a cooling tube and having an inner volume of 1,000 ml, and 242.2 g (0.80 mol) of diethyl 2-bromoterephthalate, 400 g (2.4 mol) of triethyl phosphite, and 7.09 g (0.04 mol in terms of the atoms of palladium component) of palladium chloride were added to the flask, heated to a reflux temperature and stirred at the reflux temperature for 13 hours to carry out a reaction. Time changes in the reaction were analyzed by high-speed liquid chromatography and the disappearance of the raw materials was confirmed.

After completion of the reaction, low-boiling substances such as excessive triethyl phosphite were removed by vacuum distillation. 500 g of 1,2-dichloroethane and 500 g of water were added to the residue and then an organic layer was extracted and separated by a separation operation. 1,2-dichloroethane was removed from the organic layer by vacuum distillation. The residue obtained again was distilled by vacuum distillation to obtain 183.2 g (yield of 63.9%) of diethyl 2,5-diethoxycarbonylphenylphosphonate which was an achromatic oily substance of interest.
(identification result of oily substance)
boiling point: 196° C. (1.1 mmHg)

Example 20

A magnetic stirrer was placed in a glass reaction flask equipped with a cooling tube and having an inner volume of 100 ml, and 6.60 g (0.02 mol) of diethyl 3,5-dimethoxycarbonylphenyl phosphonate obtained in the same manner as in Example 2 and 24.7 g (0.24 mol) of 35 wt % hydrochloric acid were added to the flask and heated for 8 hours under agitation and the reflux of the solvent to carry out a reaction.

After completion of the reaction, the reacted solution was concentrated by cooling and the concentrated solution was cooled with ice to deposit crystals. The concentrated solution containing deposited crystals was filtrated and the separated crystals were dried, recrystallized from methanol/dioxane (1/1 (V/V)) and dried at a reduced pressure to obtain 4.48 g (yield of 91.1%) of crystals.
(identification results of crystals)
melting point (DSC): melting start temperature: 285.3° C., peak temperature: 290.8° C., melting stop temperature: 296.2° C. MASS (FAB method) m/e (%): 247 (M$^+$1, 44), 226 (100), 225 (50), 212(36), 165 (63)
$^1$H-NMR (400 MHz, solvent: D$_6$-DMSO, reference substance: TMS)δ ppm: 8.42 (d, J=1.65, 1H), 8.45 (d, J=1.65, 1H), 8.55 (s, 1H), 13.0 to 12.1 (m, 2H)

It was confirmed from the above results that the crystals were composed of 3,5-dicarboxyphenylphoshonic acid (3,5-DPP) of interest.

Examples 21 to 28

A hydrolytic reaction was carried out in the same manner as in Example 20 by changing the type and amount of an acid or base, temperature and time. The relative area ratio (%) of 3,5-dicarboxyphenylphosphonic acid (3,5-DPP) which was the hydrolytic reaction product was obtained by the analysis of data obtained by high-speed liquid chromatography. The conditions are shown in Table 5 and the results are shown in Table 6.

TABLE 5

| Example | acid or base type | quantity (g) | solvent type | quantity (g) | reaction temperature /time (°C./h) |
|---|---|---|---|---|---|
| 21 | 35 wt % hydrochloric acid | 32.9 | none | | 100/6 |
| 22 | 47 wt % hydrobromic acid | 20.7 | none | | 110/2 |
| 23 | 97 wt % sulfuric acid | 32 | none | | 115/4 |
| 24 | 97 wt % sulfuric acid | 16 | water | 16 | 100/2 |
| 25 | sodium hydroxide | 12.7 | water | 51.3 | 100/15 |
| 26 | sodium hydroxide | 12.7 | water ethanol | 51.3 51.3 | 78/24 |
| 27 | sodium hydroxide | 12.7 | water n-butanol | 51.3 33.3 | 95/16 |

TABLE 5-continued

| Example | acid or base type | quantity (g) | solvent type | quantity (g) | reaction temperature /time (°C./h) |
|---|---|---|---|---|---|
| 28 | potassium hydroxide | 21.3 | water | 15 | 100/22 |

TABLE 6

| Example | relative area ratio obtained by HPLC 3,5-DPP (%) |
|---|---|
| 21 | 96.7 |
| 22 | 100 |
| 23 | 44 |
| 24 | 37 |
| 25 | 91 |
| 26 | 57 |
| 27 | 68 |
| 28 | 28 |

Example 29

A hydrolytic reaction was carried out in the same manner as in Example 20 except that 6.60 g (0.02 mol) of diethyl 3,5-dimethoxycarbonylphenylphosphonate in Example 20 was changed to 6.06 g (0.02 mol) of dimethyl 3,5-dimethoxycarbonyl phenylphosphonate obtained in the same manner as in Example 1 to obtain 4.41 g (yield of 89.7%) of crystals of 3,5dicarboxyphenylphosphonic acid (3,5-DPP).

Example 30

A hydrolytic reaction was carried out in the same manner as in Example 20 except that 6.60 g (0.02 mol) of diethyl 3,5-dimethoxycarbonylphenylphosphonate in Example 20 was changed to 7.18 g (0.02 mol) of di-i-propyl 3,5-dimethoxycarbonylphenylphosphonate obtained in the same manner as in Example 3 to obtain 4.54 g (yield of 92.2%) of crystals of 3,5-dicarboxyphenylphosphonic acid (3,5-DPP).

Example 31

A hydrolytic reaction was carried out in the same manner as in example 20 except that 6.60 g (0.02 mol) of diethyl 3,5-dimethoxycarbonylphenylphosphonate in Example 20 was changed to 7.74 g (0.02 mol) of di-n-butyl 3,5-dimethoxycarbonylphenylphosphonate obtained in the same manner as in Example 4 to obtain 4.52 g (yield of 91.9%) of crystals of 3,5-dicarboxyphenylphosphonic acid (3,5-DPP).

Example 32

A magnetic stirrer was placed in a glass reaction flask equipped with a cooling tube and having an inner volume of 100 ml, and 6.60 g (0.02 mol) of diethyl 2,5-dimethoxycarbonylphenylphosphonate obtained in the same manner as in Example 5 and 29.0 g (0.28 mol) of 35 wt % hydrochloric acid were added to the flask and heated for 8 hours under agitation and the reflux of the solvent to carry out a hydrolytic reaction. Crystals were deposited along with the proceeding of the reaction.

After completion of the reaction, the reacted solution was cooled at room temperature to deposit crystals. The reacted solution containing deposited crystals was filtrated, and the separated crystals were washed with 15 g of 35 wt % hydrochloric acid and then with 6 g of 2-propanol and dried at a reduced pressure to obtain 4.64 g (yield of 94.2%) of crystals.
(identification results of crystals)
melting point (DSC): melting start temperature: 298.1° C., peak temperature: 301.9° C., melting stop temperature: 307.5° C.
MASS (FD method) m/e (%): 229 ($M^+$—OH, 100)
MASS (FD method) m/e (%) (methylated product by diazomethane method): 302 (100: tetramethyl ester)
elemental analysis: actual measurement value (theoretical value) (wt %): C:39.1 (39.0), P:12.5 (12.6), H:2.92 (2.84), O:45.5 (45.5)
IR ($cm^{-1}$): 3,200 to 2,400 (OH), 1,690 (C=O)

It was confirmed from the above results that the crystals were composed of 2,5-dicarboxyphenylphosphonic acid (2,5-DPP) of interest.

Example 33

A magnetic stirrer was placed in a glass reaction flask equipped with a cooling tube and having an inner volume of 100 ml, and 7.08 g (0.02 mol) of diethyl 2,5-diethoxycarbonylphenylphosphonate obtained in the same manner as in Example 19 and 34.8 g (0.33 mol) of 35 wt % hydrochloric acid were added to the flask and heated for 8 hours under agitation and the reflux of the solvent to carry out a hydrolytic reaction. Crystals were deposited along with the proceeding of the reaction.

After completion of the reaction, the reacted solution was cooled at room temperature to deposit crystals. The reacted solution containing deposited crystals was filtrated, and the separated crystals were washed with 9 g of 35 wt % hydrochloric acid and then with 9 g of 2-propanol and dried at a reduced pressure to obtain 4.78 g (yield of 98.2%) of crystals of 2,5-dicarboxyphenylphosphonic acid of interest.

Example 34

203.4 g (0.8 mol) of bis(hydroxyethyl)terephthalate, 66.45 g (0.40 mol) of terephthalic acid and 37.22 g (0.60 mol) of ethylene glycol were charged into a 500 ml glass reactor, and the mixture in the reactor was heated at 260° C. for 3 hours under agitation in a nitrogen atmosphere at normal pressure to obtain an esterification reaction product.

The esterification reaction product, 18.25 g (74 mmol or 1.0 wt % in terms of phosphorus atoms based on produced polyester resin) of 2,5-dicarboxyphenylphosphonic acid, 0.14 g (0.5 mmol) of antimony trioxide and 0.015 g (0.06 mmol) of a cobalt acetate tetrahydrate salt were charged into the reactor and heated at 270° C. for 3 hours under agitation at normal pressure. These substances were stirred by gradually reducing the pressure to 40 mmHg and heated at 280° C. for 1 hour to carry out polycondensation, and a polyester resin was obtained.

The intrinsic viscosity [ η ] of the obtained resin was measured at 25° C. using an equivalent weight mixture of phenol and 1,1,2,2-tetrachloroethane as a solvent. The intrinsic viscosity [ η ] was 0.72 dl/g.

The flame retardancy of the obtained resin was evaluated by molding it into a test sample and measuring the flame retardancy index (oxygen index: OI) of the test sample in accordance with a flame retardancy test method (JIS D1201). The oxygen index indicating self-extinguishing properties must be at least 22. When higher flame retardancy is required, the oxygen index must be at least 27. The oxygen index of the obtained resin is 30.3 which means high flame retardancy.

Example 35

305.1 g (1.20 mols) of bis(hydroxyethyl)terephthalate and 26.58 g (1.0 wt % in terms of phosphorus atoms based on produced polyester resin) of diethyl 2,5-diethoxycarbonylphenylphosphonate were charged into a 500 ml glass reactor and heated under agitation in a nitrogen atmosphere. A reaction was carried out at 200° C. for 2 hours while ethanol and the like produced were removed by distillation at normal pressure and polycondensation was carried out at 280° C. for 1 hour by gradually reducing the pressure to 1 mmHg.

The obtained polyester resin had an intrinsic viscosity [η] of 0.70 dl/g and a oxygen index of 27.3.

When the dialkyl dialkoxycarbonylphenylphosphonate of the present invention is added as a third component to be copolymerized at the time of polyester polymerization, polyamide polymerization and polyurethane polymerization, an alcohol is eliminated from the alkoxycarbonyl group of the dialkyl dialkoxycarbonylphenylphosphonate and the alkoxycarbonyl group is changed into a carboxylic acid group to be copolymerized. When the dicarboxyphenylphosphonic acid is added as a third component to be copolymerized, it is copolymerized. As a result, a dialkoxyphosphono group or a phosphono group is introduced into the above polymer. When the introduced dialkoxyphosphono group is stable at the time of copolymerization, it remains as a dialkoxyphosphono group as it is. According to copolymerization conditions, an alcohol is further eliminated from the dialkoxyphosphono group and the group is changed into a phosphono group which serves as a crosslinking agent for a polymer. The phosphono group serves as a crosslinking agent for a polymer.

When the copolymer is processed with a fiber, the fiber having a residual dialkoxyphosphono group has improved cation dyeing properties because this functional group has cation exchange ability. A dialkoxyphosphono group which functions as a crosslinking agent in a fiber prevents shrinkage accompanied by a heat treatment and maintains the feeling of the fiber upon compounding of the fiber with other fibers.

The fiber and resin obtained from the copolymer have flame retardancy which is the characteristic property of a phosphorus-containing substance.

The dialkyl dialkoxycarbonylphenylphosphonate or dicarboxyphenylphosphonic acid of the present invention can be kneaded with a resin as a flame retardant. Illustrative examples of the resin include polyester resins, polyamide resins, polyurethane resins, polyamide resins, epoxy resins, acrylic resins and the like. A non-halogen phosphorus-containing compound such as phenylphosphonate and a triazine derivative such as melamine cyanurate have recently been used in combination to provide flame retardancy to a styrene resin.

It has been found that, in the process of the present invention for producing a dialkyl dialkoxycarbonylphenylphosphonate, a supported metal catalyst which has not been used as a catalyst in the Arbuzov reaction is used to achieve a high yield like conventionally known catalysts. Further, it has been confirmed that the supported metal catalyst can be reused. Using an alumina supported palladium catalyst in particular, an industrially advantageous process for producing a dialkyl dialkoxycarbonylphenylphosphonate can be provided.

A process for producing a dicarboxyphenylphosphonic acid can be provided due to a hydrolytic reaction of the dialkyl dialkoxycarbonylphenylphosphonate.

What is claimed is:

1. A dialkyl dialkoxycarbonylphenylphosphonate represented by the following general formula (I):

wherein $R^1$ and $R^2$ are each selected from the group consisting of alkoxycarbonyl groups having 1 to 10 carbon atoms, $R^1$ and $R^2$ are substituted at different positions arbitrarily selected from the group consisting of combinations of 2-position and 4-position, 2-position and 5-position, 2-position and 6-position, 3-position and 4-position, and 3-position and 5-position on a benzene ring, and $R^3$ is selected from the group consisting of alkyl groups having 1 to 10 carbon atoms.

2. The dialkyl dimethoxycarbonylphenylphosphonate of claim 1 which is represented by the following general formula (I):

wherein $R^1$ and $R^2$ are a methoxycarbonyl group, $R^1$ and $R^2$ are substituted at different positions arbitrarily selected from the group consisting of combinations of 2-position and 4-position, 2-position and 5-position, 2-position and 6-position, 3-position and 4-position, and 3-position and 5-position on a benzene ring, and $R^3$ is selected from the group consisting of alkyl groups having 1 to 10 carbon atoms.

3. A process for producing a dialkyl dialkoxycarbonylphenylphosphonate represented by the following general formula (I):

wherein $R^1$ and $R^2$ are each selected from the group consisting of alkoxycarbonyl groups having 1 to 10 carbon atoms, $R^3$ is selected from the group consisting of alkyl groups having 1 to 10 carbon atoms, and $R^1$, $R^2$ and $P(O)(OR^3)_2$ are substituted at arbitrarily selected different positions on a benzene ring, the process comprising heating and reacting a dialkoxycarbonylphenyl halide represented by the following general formula (II):

wherein $R^4$ and $R^5$ are each selected from the group consisting of alkoxycarbonyl groups having 1 to 10 carbon atoms, X is a halogeno group, and $R^4$, $R^5$ and X are substituted at arbitrarily selected different positions on a benzene ring, with a trialkyl phosphite represented by the following general formula (III):

(R⁶O)₃P        (III)

wherein $R^6$ is selected from the group consisting of alkyl groups having 1 to 10 carbon atoms, in the presence of a catalyst comprising an element of group VIII of the periodic table.

4. A process for producing a dialkyl dialkoxycarbonylphenylphosphonate according to claim 3, wherein the catalyst comprising an element of group VIII of the periodic table is at least one catalyst selected from the group consisting of palladium catalysts and nickel catalysts.

5. A process for producing a dialkyl dialkoxycarbonylphenylphosphonate according to claim 3, wherein the catalyst comprising an element of group VIII of the periodic table is at least one catalyst selected from the group consisting of supported palladium catalysts and supported nickel catalysts.

6. A process for producing a dialkyl dialkoxycarbonylphenylphosphonate according to claim 3 which uses at least one solvent selected from the group consisting of aromatic hydrocarbons and ethers.

7. A process for producing a dicarboxyphenylphosphonic acid represented by the following general formula (IV):

wherein $R^7$ and $R^8$ are each a carboxyl group, and $R^7$, $R^8$ and $P(O)(OH)_2$ are substituted at arbitrarily selected different positions on a benzene ring, the process comprising heating and reacting a dialkoxycarbonylphenyl halide represented by the following general formula (II):

wherein $R^4$ and $R^5$ are each selected from the group consisting of alkoxycarbonyl groups having 1 to 10 carbon atoms, X is a halogeno group, and $R^4$, $R^5$ and X are substituted at arbitrarily selected different positions on a benzene ring, with a trialkyl phosphite represented by the following general formula (III):

(R⁶O)₃P        (III)

wherein $R^6$ is selected from the group consisting of alkyl groups having 1 to 10 carbon atoms, in the presence of a catalyst comprising an element of group VIII of the periodic table to obtain a dialkyl dialkoxycarbonylphenylphosphonate represented by the following general formula (I):

wherein $R^1$ and $R^2$ are each selected from the group consisting of alkoxycarbonyl groups having 1 to 10 carbon atoms, $R^3$ is selected from the group consisting of alkyl groups having 1 to 10 carbon atoms, and $R^1$, $R^2$ and $P(O)(OR^3)_2$ are substituted at arbitrarily selected different positions on a benzene ring, and hydrolyzing the dialkyl dialkoxycarbonylphenylphosphonate in the presence of an acid or base.

8. The process for producing a dicarboxyphenylphosphonic acid according to claim 7, wherein the acid is at least one inorganic acid selected from the group consisting of hydrochloric acid and hydrobromic acid.

9. The process for producing a dicarboxyphenylphosphonic acid according to claim 7, wherein the base is at least one inorganic base selected from the group consisting of sodium hydroxide and potassium hydroxide.

* * * * *